US011008195B2

(12) United States Patent
Lucas (10) Patent No.: US 11,008,195 B2
(45) Date of Patent: May 18, 2021

(54) PORTABLE, POWERED COLLECTION SYSTEM FOR FLEXIBLE FLUID HOSES

(71) Applicant: Timothy Craig Lucas, Bixby, OK (US)

(72) Inventor: Timothy Craig Lucas, Bixby, OK (US)

(*) Notice: Subject to any disclaimer, the term of this patent is extended or adjusted under 35 U.S.C. 154(b) by 152 days.

(21) Appl. No.: 16/483,003

(22) PCT Filed: May 23, 2018

(86) PCT No.: PCT/US2018/034225
§ 371 (c)(1),
(2) Date: Aug. 1, 2019

(87) PCT Pub. No.: WO2018/217949
PCT Pub. Date: Nov. 29, 2018

(65) Prior Publication Data
US 2019/0367321 A1    Dec. 5, 2019

Related U.S. Application Data

(60) Provisional application No. 62/510,302, filed on May 24, 2017.

(51) Int. Cl.
*B65H 75/36*    (2006.01)
*B65H 51/10*    (2006.01)
(Continued)

(52) U.S. Cl.
CPC ....... *B65H 75/362* (2013.01); *A61M 16/0672* (2014.02); *A61M 16/101* (2014.02);
(Continued)

(58) Field of Classification Search
CPC ........ B65H 49/02; B65H 51/04; B65H 51/10; B65H 51/28; B65H 51/32; B65H 54/76;
(Continued)

(56) References Cited

U.S. PATENT DOCUMENTS 2,670,926 A    3/1954 Sewell
3,028,834 A    4/1962 Klein
(Continued)

FOREIGN PATENT DOCUMENTS

GB    1549791 A  *  8/1979  ............. B66D 3/003

OTHER PUBLICATIONS

Lee W. Young, Written Opinion of the International Searching Authority, PCT/US2018/034225, dated Oct. 17, 2018, pp. 1-12, IPEA/USPTO, Alexandria VA, USA.
(Continued)

*Primary Examiner* — Michael McCullough
(74) *Attorney, Agent, or Firm* — Rylander & Associates, PC; Philip R. M. Hunt (57) ABSTRACT

The present invention relates generally to medical equipment, more particularly, the use of fluid hoses coupling tanks to cannulas, as part of medical gas therapy, such as oxygen therapy. The invention describes a collection system for managing excess flexible hose that a patient might need to wear for medical reasons such as home oxygen medical therapy. It comprises a non-spooling roller system attached to a receptacle for collecting excess hose into the receptacle and extraction from the receptacle, and a power system to power and control the roller system, and design features that optimize the collection and extraction.

15 Claims, 6 Drawing Sheets

(51) Int. Cl.
*A61M 16/06* (2006.01)
*A61M 16/10* (2006.01)

(52) U.S. Cl.
CPC ......... *B65H 51/10* (2013.01); *A61M 2209/08* (2013.01); *B65H 2701/33* (2013.01)

(58) Field of Classification Search
CPC .... B65H 76/36; B65H 76/362; B65H 76/364; B65H 76/366; B65H 76/368; B65H 2701/33; A61M 39/08
See application file for complete search history.

(56) References Cited

U.S. PATENT DOCUMENTS

| | | | | |
|---|---|---|---|---|
| 3,750,970 | A | * | 8/1973 | Tremoulet, Jr. ....... A01K 73/06 242/361.4 |
| 3,901,426 | A | * | 8/1975 | Zatopek ................ B65H 51/10 226/134 |
| 4,343,420 | A | | 8/1982 | Scott |
| 4,541,615 | A | | 9/1985 | King, Jr. |
| 4,692,569 | A | | 9/1987 | Winner |
| 4,739,913 | A | | 4/1988 | Moore |
| 4,853,500 | A | * | 8/1989 | Tydlacka ............. B65H 75/362 191/12 R |
| 5,332,171 | A | | 7/1994 | Steff |
| 6,109,544 | A | | 8/2000 | Sheng |
| 6,427,284 | B1 | | 8/2002 | Harrelson, II |
| 7,285,111 | B2 | | 10/2007 | Gaster |
| 7,487,791 | B1 | | 2/2009 | Bradley |
| 7,690,544 | B2 | * | 4/2010 | Zaruba .................. B65H 57/14 226/186 |
| 7,973,516 | B2 | | 7/2011 | Flack |
| 8,028,834 | B2 | | 10/2011 | Lill |
| 10,214,378 | B2 | * | 2/2019 | Bortz ....................... D07B 7/10 |
| 10,441,772 | B2 | * | 10/2019 | Lucas ................ A61M 16/101 |
| 2005/0028493 | A1 | | 2/2005 | Small |
| 2006/0243282 | A1 | | 11/2006 | Sackman |
| 2008/0061184 | A1 | * | 3/2008 | Simbirski ............. B65H 54/76 242/526 |
| 2008/0210236 | A1 | | 9/2008 | Richard |
| 2009/0205991 | A1 | | 8/2009 | Lill |
| 2010/0307496 | A1 | | 12/2010 | Lueckenhoff |
| 2012/0152926 | A1 | | 6/2012 | Matiash |
| 2015/0075528 | A1 | | 3/2015 | Kudo |
| 2015/0237933 | A1 | | 8/2015 | Abshire |
| 2016/0060075 | A1 | | 3/2016 | Slowik |
| 2016/0354570 | A1 | | 12/2016 | Arroyo |

OTHER PUBLICATIONS

Product for Sale: Green Leaf Wonder Winder Extension Cord Winding System—Model# WW 2D website #1: https://www.northerntool.com/shoptools/product_200610485_200610485 website #2: https://www.amazon.com/Green-Leaf-WW-1-Wonder-Extension/dp/B00005A1K1.

* cited by examiner

PORTABLE, POWERED COLLECTION SYSTEM FOR FLEXIBLE FLUID HOSES

CROSS-REFERENCE TO RELATED APPLICATIONS

The invention claims priority of U.S. provisional patent application No. 65/510,302, filing date 24 May 2017, titled: Portable, Powered, Remote Control Tube Handling System For Flexible Hoses.

This invention references and is related to U.S. provisional patent application No. 62/297,828, filing date 20 Feb. 2016, titled: Flexible Tube and Hose Management System; and subsequent U.S. utility patent application Ser. No. 15/436,789, filing date 18 Feb. 2017, titled: Portable, Powered Collection System for Flexible Fluid Hoses.

BACKGROUND OF THE INVENTION

Technical Field

The field of the invention is ancillary devices for patient medical care, particularly bags or receptacles for storing, carrying and managing fluid hose.

Chronic Obstructive Pulmonary Disease (COPD) is a group of diseases—which includes emphysema and chronic bronchitis—which cause breathing-related problems and airflow restriction. According to the U.S. CDC, approximately 16 million Americans have been diagnosed with COPD (almost 7% of the population). The number of people with this condition is presumably much higher: the COPD Foundation estimated the total number affected at 30 million, which is generally in line with the NIH (which estimated 12 million undiagnosed COPD cases in 2012).

Worse yet, chronic lower respiratory disease is the third leading cause of death in the U.S., with COPD causing over half of the deaths from lung diseases. [source: NIH's National Heart Lung and Blood Institute. 2012 Morbidity and Mortality: Chart Book on Cardiovascular, Lung, and Blood Diseases. https://www.nhlbi.nih.gov/research/reports/2012-mortality-chart-book]

COPD is costly. The CDC estimated that the costs attributable to having COPD were approximately $32 billion in 2010, paid as follows: the Medicare system paid 51%, the Medicaid system paid 25% and private insurers paid 18%. "By 2020 it is expected that the cost of medical care for adults with COPD will be more than $90 billion . . . " [source: CDC website.]

For people with COPD or similar condition, oxygen therapy is often prescribed by their doctors for the related medical conditions. In fact, about 14% of patients are prescribed oxygen therapy. [source: Direct costs of chronic obstructive pulmonary disease among managed care patients, Anand A Dalal, Laura Christensen, Fang Liu, and Aylin A Riedel, Int J Chron Obstruct Pulmon Dis. 2010; 5: 341-349. https://www.ncbi.nlm.nih.gov/pmc/articles/PMC2962300]

Out of the total of $32 billion, the U.S. Medicare system spends a great deal on home oxygen equipment itself. According to the NIH's National Heart, Lung, and Blood Institute and the Centers for Medicare and Medicaid Services in 2004, "Total Medicare reimbursements for costs related to [oxygen therapy] exceed $2 billion/year and are increasing at an annual rate of 12 to 13%." [source: Long-term Oxygen Treatment in Chronic Obstructive Pulmonary Disease: Recommendations for Future Research, Thomas L. Croxton, William C. Bailey, American Journal of Respiratory and Critical Care Medicine Vol 174. pp. 373-378, 2006. https://www.nhlbi.nih.gov/research/reports/2006-oxygen-treatment] [Back in 1997, Medicare was spending $1.8 billion annually for home oxygen equipment for COPD, so the pace appeared to accelerate. Source: Long-Term Oxygen Therapy: New insights and perspectives, pp 221-232, Chapter 19: The Economic Impact of Long-Term Oxygen Therapy Lorenzo G. Mantovani, Marco Cristiani, Gianluca Furneri. 2012.]

The National Home Oxygen Patients Association claimed in 2012 that over one million people used supplementary oxygen but considering an estimated 800,000 people used home oxygen in 1995, presumably, the numbers are substantially higher now [Source: O'Donohue W J and A L Plummer, Magnitude of usage and cost of home oxygen therapy in the United States, Chest 107: 301-302, 1995].

There are three common sources of medical oxygen: concentrators, compressed gas, or liquid. All three require the user to pull around a wheeled tank or carry or pull a concentrator unit.

All three require the use of oxygen tubing/hose from the tanks or concentrator to the patient's cannula. The tubing or hose that connects to the concentrator and then to the patient can easily become tangled and hinder free and easy movement of the patient.

Loose hose underfoot poses a tripping threat that could lead to the patient—or others—falling. Loose hose also increases the potential of kinking, pinching, or other obstruction of the hose and its gas flow. These risks are amplified if the patient has mobility issues and/or uses a walker, cane or wheelchair in addition to medical gas therapy equipment. In hospital and at home, extra hose is sometimes looped and hung from IV stands or tank carts, or even draped over the tanks themselves, practices which have the same drawbacks.

BACKGROUND ART

Some current methods to address this loose or excess hose problem are expensive and not easily maintained, nor are they easy to install or set up. They can be large and/or heavy. Some are not simple or intuitive. Some methods rely on a spool to wrap the hose around, which can lead to pinching and kinking of the hose. Spooling increases twisting of hose, by forcing it in a fixed position around a spool. Spooling methods add bulk as well, because of the spindle diameter. See, e.g., US Patent Application 2005/0028493 A1, published Feb. 10, 2005, from Small.

Other methods rely on ceiling-mounted devices that are difficult to install, use, and maintain and are far less mobile than a movable container. Other methods available manage excess hose by means of an accordion type jacket or gather placed around a section of the excess hose, which is an imperfect solution because of device bulk; the device can itself become a hazard. See, e.g., US Patent Application 2015/0075528 A1, published Mar. 19, 2015, from Kudo, which shows how a gather will apply continual pressure on the patient because the device itself can create hazardous or inconvenient tension or "springiness," as noted in that application. And that type of solution can prevent the patient from using both hands for other tasks.

Another method is to use a soft-sided sack used to collect hose, such as U.S. Pat. No. 4,739,913, issued Apr. 26, 1988, to Moore and U.S. Pat. No. 8,028,834 B2, issued Oct. 4, 2011, to Lill. However, using only a flexible fabric bag leads to bunching and twisting of the hose while in the container and can lead to pinching and kinking of the hose, and which causes difficulty when extracting the hose from the bag.

Some soft-bag methods try to get around the bunching and twisting issues inherent in soft side bags by teaching using a single, typically centered, rib to provide some structure to a soft hose bag, but this solution does little to maintain the interior volume of the collection container, other than to keep constant the distance from the bag's top to bottom.

Extraction is also an issue with soft bags, as they are particularly problematic in an emergency situation, when it's necessary to remove the hose from the bag quickly and untangle it. Anyone who has quickly pulled items from a soft-sided backpack can attest to this, particularly when it's on the person's back.

Other alternative methods include hard-sided cases for hose, such as U.S. Pat. No. 7,487,791 B1, issued Feb. 10, 2009 to Bradley. This method is best suited to collecting loose hose one time, but poorly suited to repeated collection and extraction because the hose is essentially clipped in place.

Further, these bagging or clipping methods do not offer functional means of collecting the hose into the bag, other than manually stuffing the hose in by hand.

The invention disclosed in the related application, U.S. utility patent application Ser. No. 15/436,789, filing date 18 Feb. 2017, to Lucas, titled: Portable, Powered Collection System for Flexible Fluid Hoses had several improvements over the prior art, including disclosing a non-spooling, powered roller system to collect and extract hose from a collection container. It taught a mechanism which avoided the drawbacks of the prior art, as enumerated above, and provided an inexpensive, portable, functional system for maintaining loose hose.

The present invention is a further improvement over the prior art. Like Lucas application '789, it avoids the kinking and twisting of hose collected in soft bags lacking a frame. It avoids spooling hose around a spindle. It maximizes the smooth collection of hose into and out of a container, here, a receptacle. It prevents the user from needing to carry around heavy equipment. It seeks to offer a low cost, easy to manufacture, easy to maintain and use system that more completely manages the problem of excess hose for the patient or a person who wants to make sure hose is safely collected and not underfoot. As improvements over Lucas application '789, it further allows the stationary use of commonly available, readily purchased, inexpensive receptacles, and improves upon the collection and extraction of the hose, including by optimizing the positioning of the hose during extraction and collection.

BRIEF DESCRIPTION OF DRAWINGS

Having thus described the invention in general terms, reference will now be made to the accompanying drawings, which are not necessarily drawn to scale.

FIG. 5. is top, side perspective, close-up views of the upper part of the roller system in two positions, closed, FIG. 5A, and open, FIG. 5B.

FIG. 6 shows two views of the anchoring mechanism by itself, with FIG. 6A, showing a top, side perspective view, and FIG. 6B, showing a side view, shown with the anchoring mechanism hung over a receptacle wall, with the hose and swivel in place, with neither the swivel nor hose claimed.

DETAILED DESCRIPTION OF THE INVENTION

Before beginning a detailed description of the subject invention, mention of the following is in order. When appropriate, like references are used to designate identical, corresponding, or similar components in different figure drawings. The figure drawings associated with this invention are not drawn with strict dimensional accuracy, i.e., the drawings have been drafted with a focus on clarity of viewing and understanding rather than strict dimensional accuracy.

For all of the components in this invention, it is preferable that the components be as small, light-weight, and portable as possible, taking into consideration cost of materials and manufacture. This is preferable to make the invention portable, durable, and light-weight, so it can be used by a patient or others and be constructed using components which are cost-effective.

Figure 1:
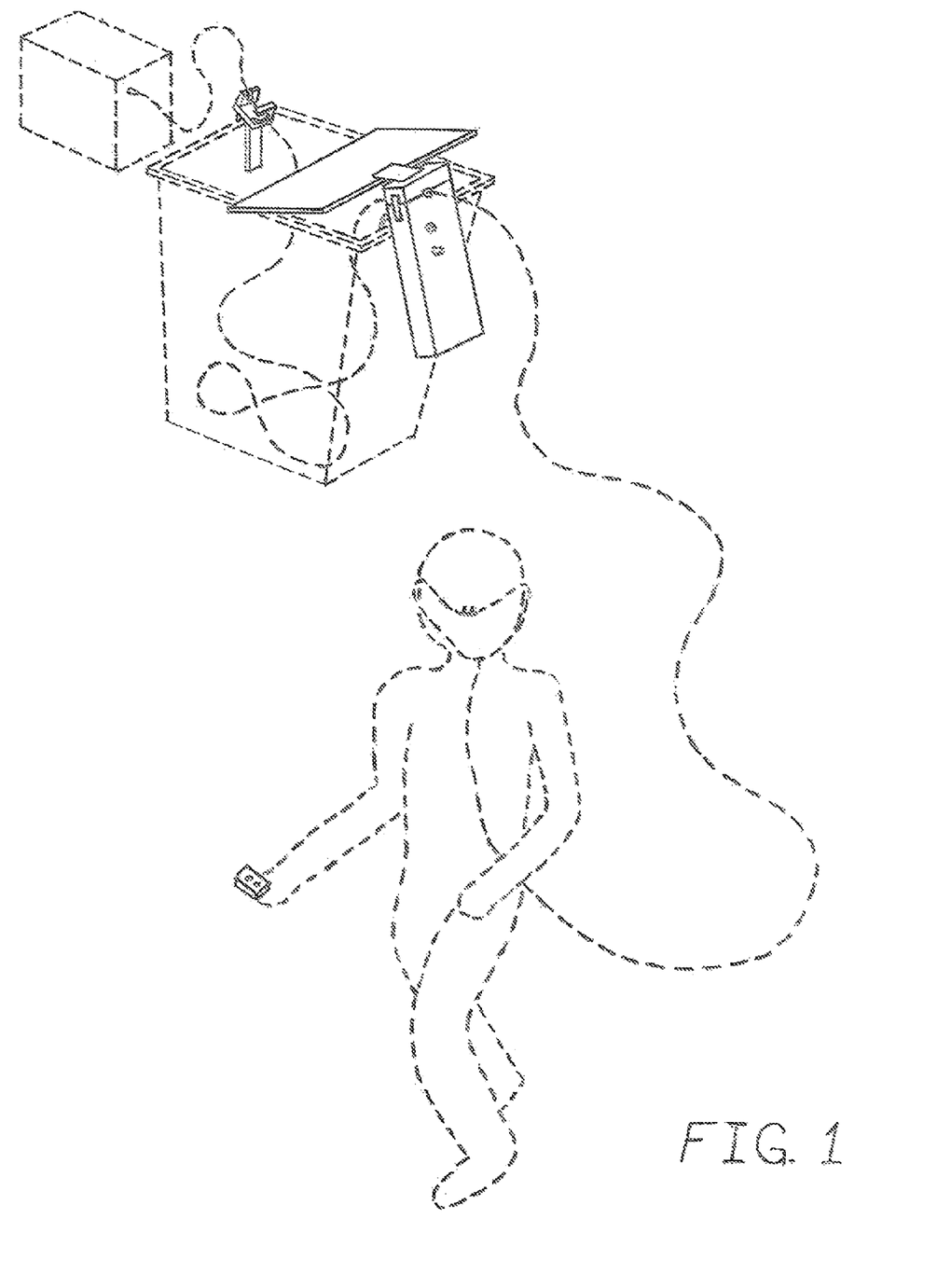
FIG. 1 shows a top, side perspective view of the invention in use, with both the anchoring mechanism and roller system attached to a receptacle, and a patient wearing a cannula and oxygen hose also connected to an oxygen concentrator and holding a remote-control unit. The patient, concentrator, and hose are not claimed in this disclosure, and are shown only for reference in the Figures, in dashed lines.
Figure 2:
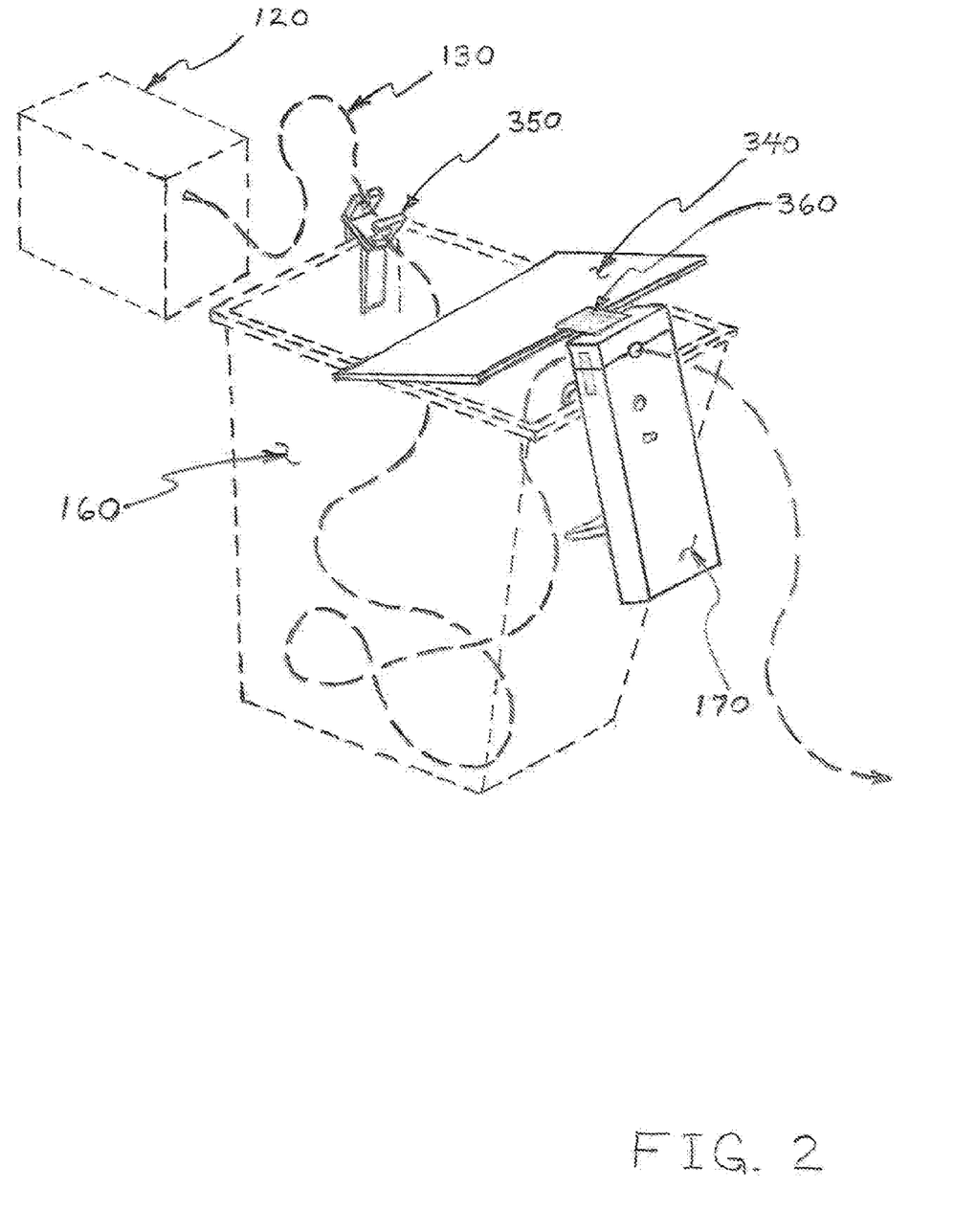
FIG. 2 shows a top, side perspective view of the roller system and anchoring mechanism attached to a receptacle, with the hose connected to an oxygen concentrator, and a top guard over the receptacle. Once again, the hose and concentrator are not claimed.

Referring now to the invention in more detail, FIG. 1 shows a patient alongside the invention. Here, as in FIG. 2, an oxygen concentrator 120 has hose 130 coming out of it and running through the anchoring mechanism 350, into the receptacle 160, and up through the roller system 170 the hose continues, up to the cannula on the patient. The hose, the patient, the cannula, and the oxygen concentrator are not claimed, but are shown for reference in dashed lines. A receptacle 160 is shown in FIGS. 1, 2, and 6B, and is to be used with the invention, but the specific shape and dimensions of the receptacle are not claimed, and a receptacle is represented in the figures using dashed lines because of this.

The roller system's fundamentals and interior mechanisms were disclosed and detailed in U.S. provisional patent application No. 62/297,828, to Lucas, filing date 20 Feb. 2016, titled: Flexible Tube and Hose Management System; and subsequent U.S. patent application Ser. No. 15/436,789, to Lucas, filing date 18 Feb. 2017, titled: Portable, Powered Collection System for Flexible Fluid Hoses. All internal roller system elements described within that disclosure are incorporated herein for reference and are not detailed herein.

Unlike the prior invention, however, the roller system in this disclosure is attached to a receptacle like a standard, inexpensive, readily available office trash bin. The collection container detailed in the prior Lucas '789 application is replaced by this rigid receptacle. The roller system 170 is attached to one side of the receptacle, and the anchoring mechanism 350 is attached to the other side of the receptacle, as shown in FIGS. 1, 2 and 6B.

Figure 3:
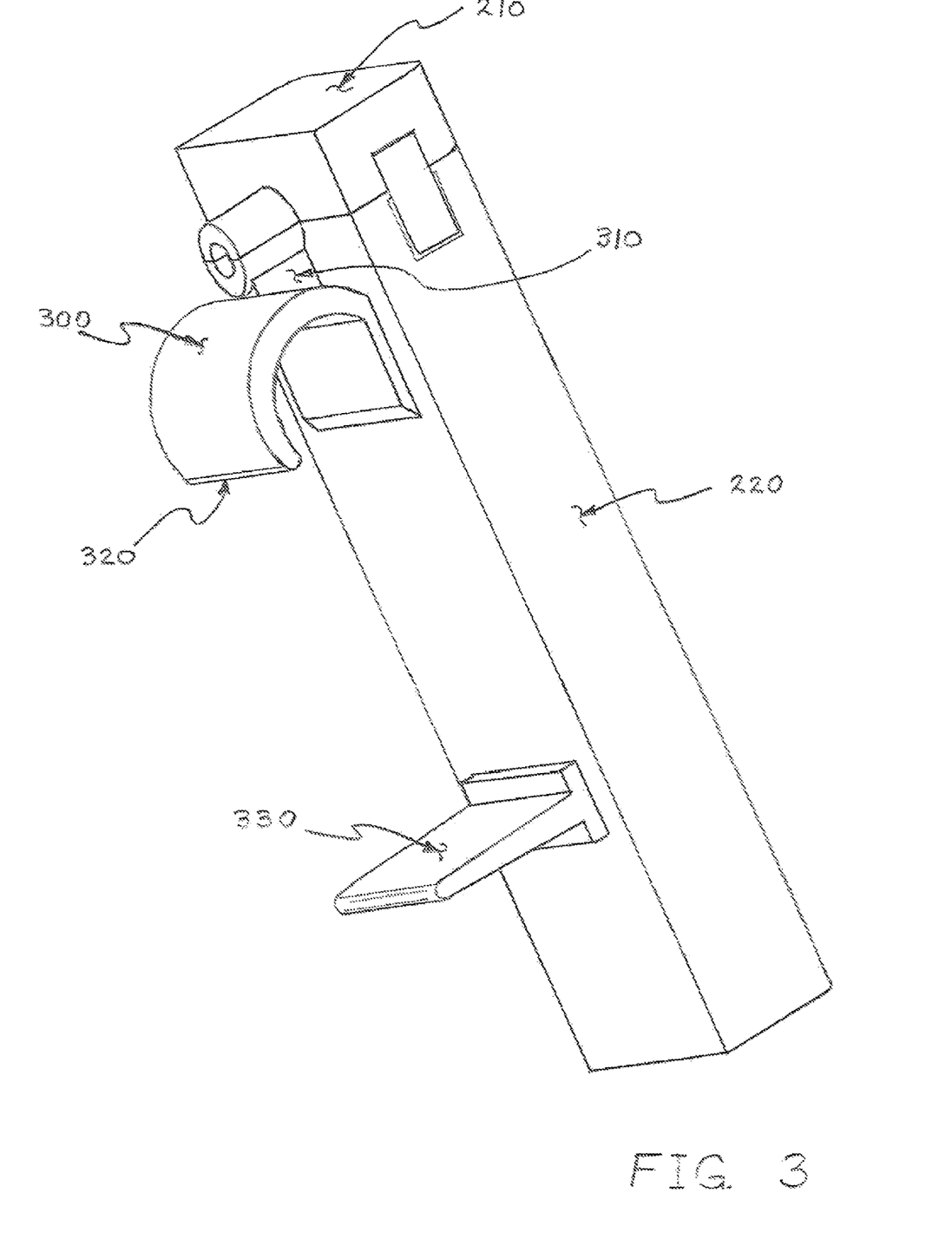
FIG. 3 shows a top, side perspective of the roller system by itself, showing the external features.
Figure 4:
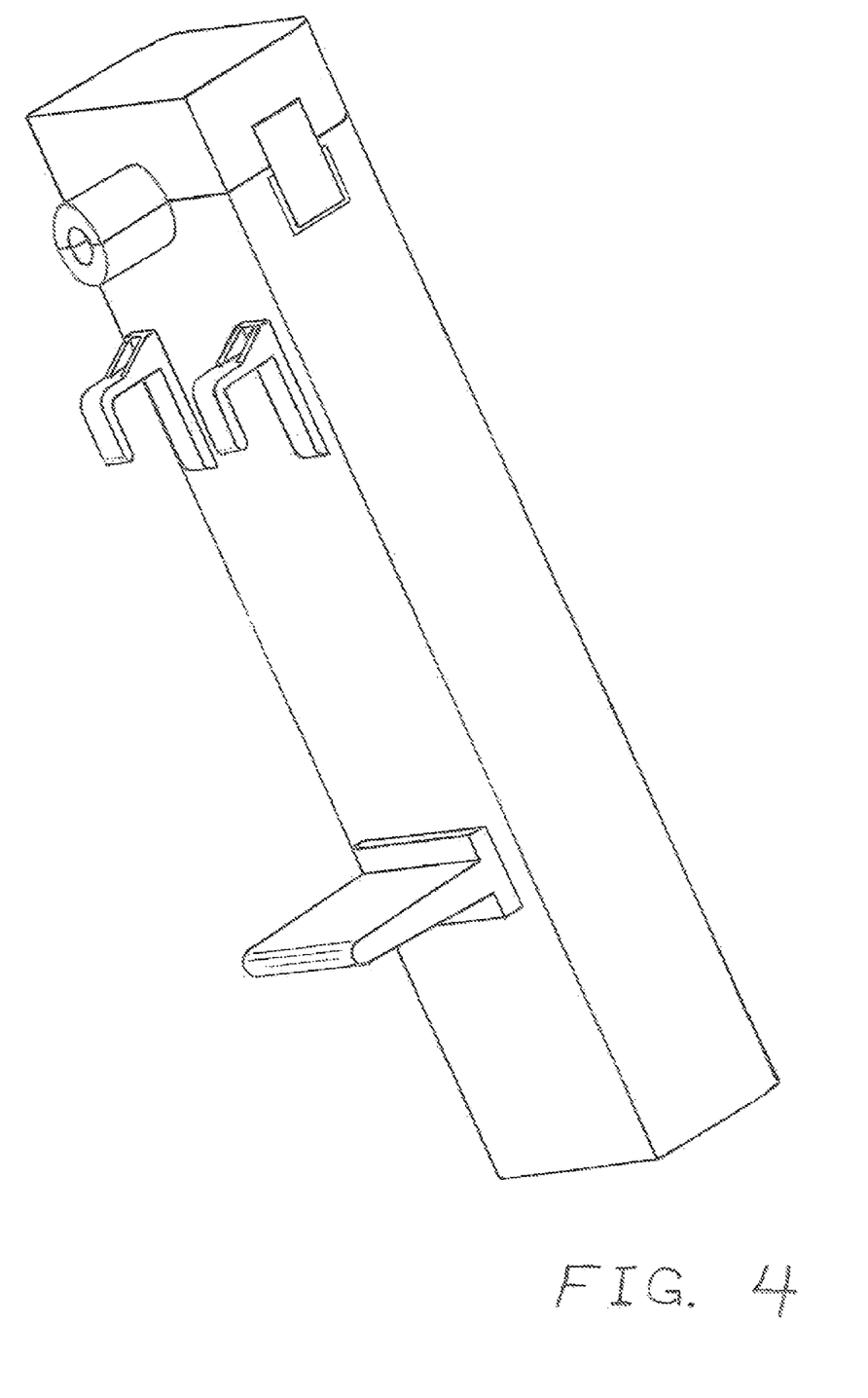
FIG. 4 shows a top, side perspective of the roller system by itself, showing the external features on an alternative embodiment.
Figures 5, 5B:
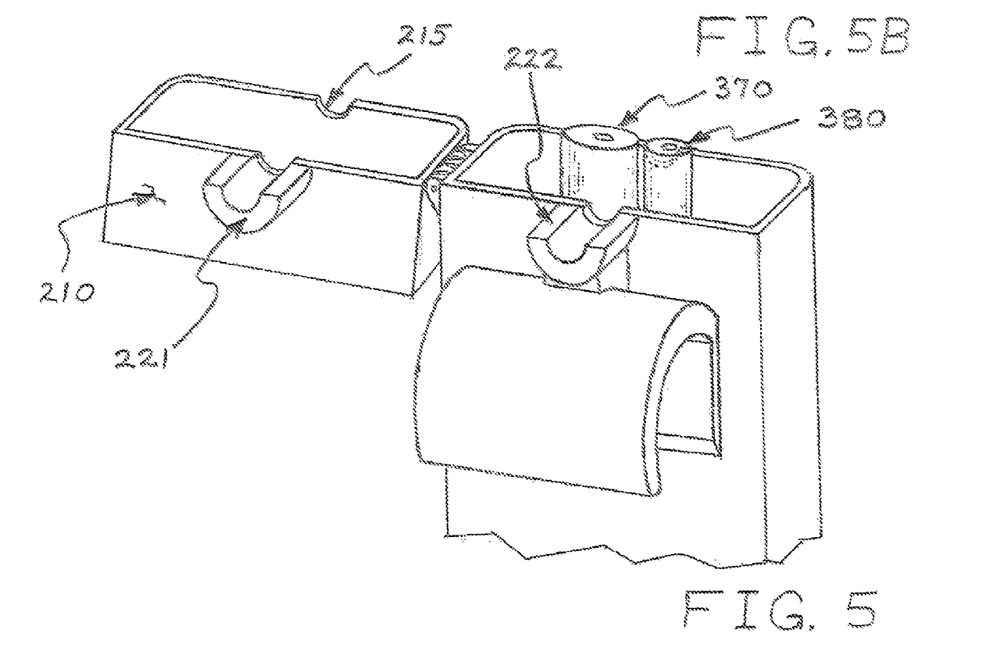
Figures 6, 6B:
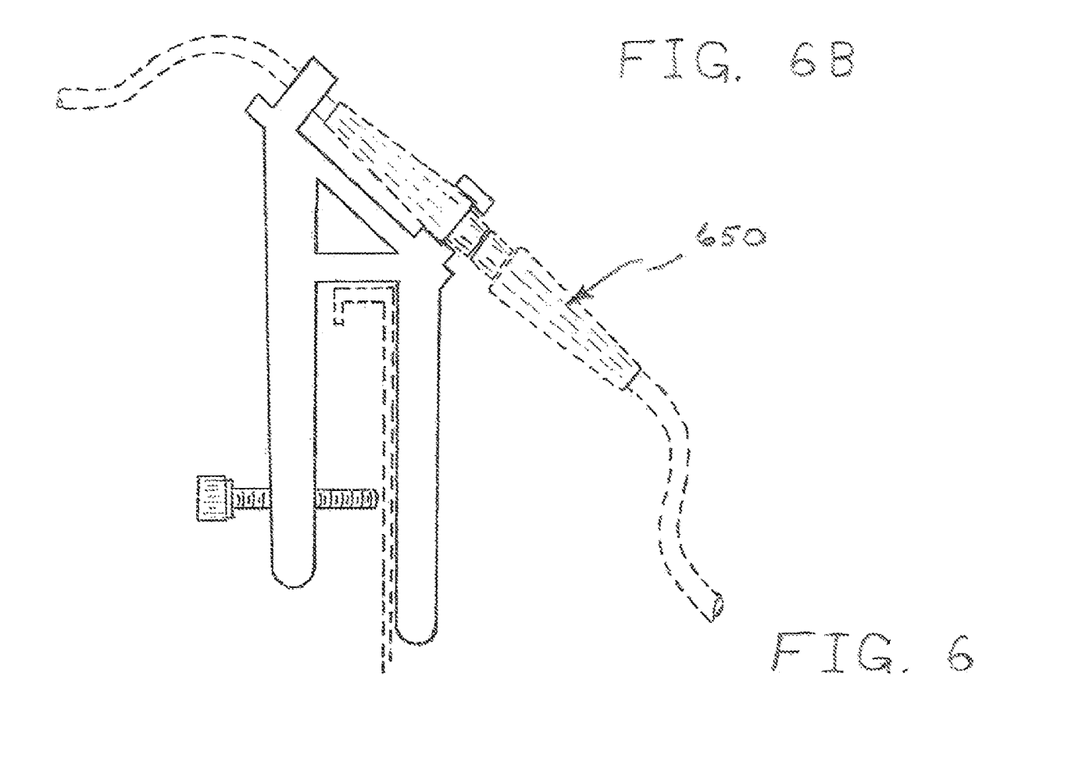
Figure 6A:
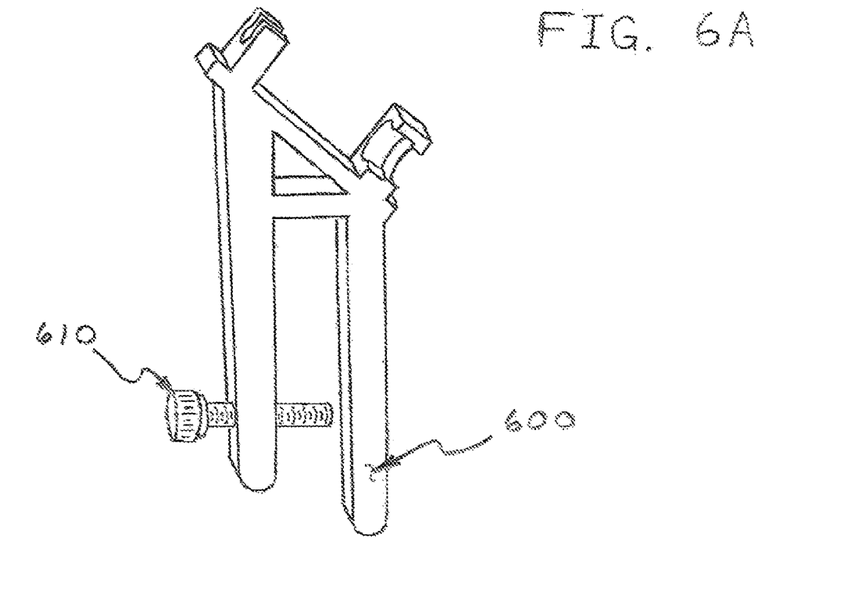

FIGS. 3, 4, and 5 show only the roller system 170 and FIG. 6 shows only the anchoring mechanism 350.

There are several essential elements in the present invention. First, the roller system disclosed in the prior Lucas '789 application is not attached to a bag, but rather is hung on or attached to the side of a receptacle. The internal workings of the prior-disclosed roller system can be the same as in the prior application, but new, external features are added to dramatically improve the operation of the system. The added features promote the smooth intake and exit of the hose into and from the roller system and further prevent the hose from tangling or twisting on the roller system.

In the main embodiment described herein, the roller system is removably attached to the outside, top lip of a receptacle.

There are two additional, overall improvements made to the exterior of the roller system 170 that help guide the hose into the opening of the roller system: a means of preventing the hose from looping over the top of the roller system, and a means of preventing the hose from getting hung up below in the opening of the roller system. A third improvement in the opening itself improves intake performance. A fourth improvement helps to create a preferable angle for the hose as it enters/exits the roller system.

A fifth improvement of this invention, an anchoring mechanism, is used on the receptacle, holding the hose between the oxygen concentrator and the receptacle. The design of the anchoring mechanism includes angling and anchoring improvements.

Figure 5A:
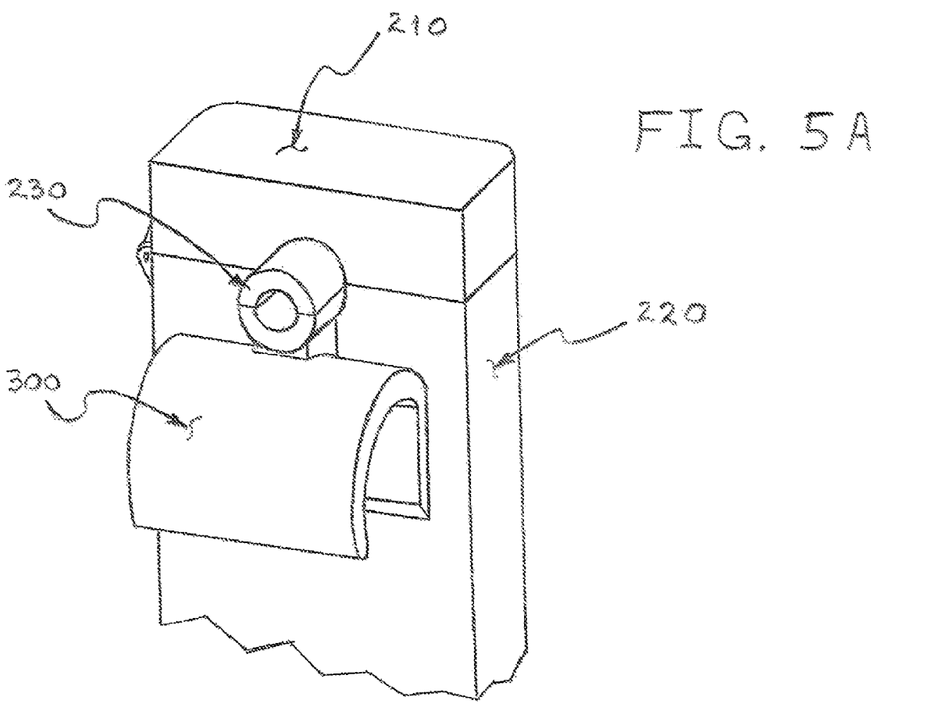

FIG. 5A shows the hose guide 210 of the roller system in a "closed" position. FIG. 5B shows the hose guide 210 in an "open" position. Like in the prior application (application '789, to Lucas), the hose is threaded between the two rollers by the user and the roller guide is then closed and covers the rollers. The hose sticks out through a cut-out 215 made by the hose guide and the housing. As in that prior application, the hose guide should be designed so that it could be opened and closed readily to allow the user to install and uninstall the hose as desired.

As in the prior application (application '789, to Lucas), the hose guide 210 can be constructed of many different materials but requires sufficient rigidity to keep the hose straight and unkinked as it is drawn into or released from the receptacle 160. Lightweight, rigid, injection-molded plastic is used in the embodiment, because of its weight, durability, and ease of manufacture. Other materials can be used, but at the risk of sacrificing these desirable characteristics.

As in the prior application (application '789, to Lucas), the dimensions of the cut-out 215 in the hose guide 210 are dependent on the diameter of the hose 130 that the invention is designed for. The cut-out's diameter must be sufficiently wide enough, and its edges must be sufficiently rounded so as to prevent cutting or scraping or damage to the hose when used. The cut-out's dimension must be wide enough to accommodate hoses of various diameters, but not be overly wide, such that it does not allow kinked or knotted hose to enter the hose guide 210 and does not allow the hose to escape its proper positioning between the rollers. The cut-out should be a minimum of 8 mm in interior diameter to accommodate the most common oxygen hoses.

On the receptacle side of the hose guide, instead of a simple cut-out in the hose guide, a tubular guide 230 is created when the hose guide and housing 220 are in the "closed" position. This tubular guide is labeled on FIG. 5B by its top channel 221 and bottom channel 222 elements.

When closed, the tubular guide is hollow shaft with an interior diameter larger than the diameter of the cut-out 215. Away from the rollers, the shaft's exit diameter is preferably two to three times wider than the diameter of the cut-out.

The interior shaft of the tubular guide can preferably be conical, such that the diameter increases from the cut-out diameter to the exit diameter. Having a tubular guide shaft diameter greater than the cut-out diameter helps to smooth hose kinks as the hose enters the roller system.

A similar tubular guide could alternatively be added on the cut-out side of the roller system but is not necessary to smooth functioning of the roller system and conveys insignificant advantage in practice.

Beneath the tubular guide, there is a bracket 300 that removably attaches the roller system to the receptacle, fitting over the lip of the receptacle (as shown in FIGS. 1, 2, 5, and 6B). The gap between the bracket and the tubular guide is preferably filled in with support material 310 (FIGS. 3, 5A and 5B) to prevent the hose from becoming lodged between the bracket 300 and the bottom channel element 222. The support material provides additional rigidity to both the tubular guide and the bracket.

FIG. 4 shows an alternative embodiment wherein the single bracket of FIG. 3 is split into two separate brackets, in order to save material cost. This also reduces the advantage of using support material 310.

The outer edge of the underside of the bracket opposite the housing, labeled in FIG. 3 as 320 must be sufficiently far enough from the housing 220, such that the bracket can be placed over the top lip of a receptacle. It can accommodate various widths of the top lips on various receptacles, and should, at a minimum, be capable of fitting over a lip of width greater than 1 cm. In practice, the top lip of the most commonly sold office-style trash receptacle is approximately 13 mm. Further, the outer edge 320 should, when placed over the top lip of a receptacle, be preferably extended downward more than 25 mm from the receptacle's top lip, to sufficiently hang or attach the roller system onto the lip of the receptacle, so that it doesn't dislodge during repeated use.

Just for reference, FIG. 5B shows the drive roller 370 and the idler roller 380, but no other internal components of the roller system. Those components were disclosed in the prior application (application '789, to Lucas) and incorporated by reference as noted above.

Inexpensive, commonly available receptacles typically taper narrower from their opening toward their bottom resting on the floor; as such, their side walls are not strictly vertical and perpendicular to the floor. This tapering is illustrated in FIGS. 1 and 2. When the invention is placed on a receptacle, the housing 220, should be perpendicular to the floor or at an acute angle to the floor, or if an imaginary line were drawn through the cut-out and the through tubular guide, it would be horizontal to the floor at a minimum, or angled downward into the receptacle. To accomplish this in the preferred embodiment while using a commonly available, tapering receptacle, it is preferable to hold the housing away from the side of the receptacle; the bottom of the housing must be tilted away from the outer wall of the receptacle.

In the preferred embodiment, this is accomplished through the use of a brace 330. As shown in FIG. 3, this brace 330 is mounted to the lower half of the housing 220 and creates space between the outer wall of the receptacle and the housing. The exact placement of the brace on the body of the housing and the side-to-side width of the brace is not essential. However, the brace must create enough space between the housing and the outer wall of the receptacle such that the housing is horizontal to the floor at a minimum, or, more preferably, the exit hole of the tubular guide is situated below the cut-out and points slightly downward into the receptacle. The exact angle the tubular guide drops below the horizontal is not essential, but the downward or depression angle of the tubular guide is generally between zero and 45 degrees, preferably greater than 5 degrees. The brace shown in FIGS. 3 and 4 would stick out from the roller system housing approximately 4 cm.

It is alternatively possible to create the depression angle tilt of the hose downward into the receptacle not by angling the entire roller system housing as in the preferred embodiment, but by angling only the cut-out and tubular guide downward.

Although not essential to the present invention, after the roller system is attached to the receptacle, a top guard 340 should preferably be attached above the tubular guide. The preferred embodiment of this top guard is shown in FIGS. 1 and 2. For simplicity and ease of construction, it is preferably a flat piece of rigid material and can be removably attached to the top of the hose guide, preferably with a strip of Velcro 360. It can be constructed of the same material as the housing, to save costs. The top guard would preferably be as wide as the side-to-side width of the receptacle, so it can rest on the top of the receptacle, on the receptacle's top lips. This top guard serves to keep the hose down within the receptacle and thereby provide additional guidance for the hose as it enters and exists the tubular guide, and further prevents kinking of the hose. It should not impede or press down on, or add friction to, the hose at the point it enters or exits the tubular guide.

As shown in FIGS. 1 and 2, an anchoring mechanism 350 is attached to the side of the receptacle opposite the main roller system. This anchoring mechanism serves several functions, first, to anchor the hose to the receptacle, as it leaves the oxygen concentrator, as shown in FIGS. 1 and 2. Second, it is an angled bracket, as seen more readily in FIG. 6, and it directs the hose downward into the receptacle, while holding it in place. Like the bracket mounting the roller system, the anchoring mechanism should be wide enough to fit over the lip of the receptacle, and tall enough so that when it is placed on the receptacle, over the top lip of the receptacle, that it will not be easily dislodged during use of the roller system. Like the roller system, the anchoring mechanism should be capable of being removed from the receptacle, so it can be used on another receptacle.

Further, in the preferred embodiment, the anchoring mechanism should be constructed to hold in place a connector, such as the commonly available, standard oxygen tubing swivel connector 650, as shown in FIG. 6B. The swivel connector itself is not claimed but shown for reference and placement. By accommodating a swivel connector, the anchoring mechanism can add the functionality of lessening kinking and twisting of the hose in the receptacle during operation because of the back-and-forth play in the swivel connector, as it holds the hose to the receptacle. The anchoring mechanism should be constructed so as to not impede the swiveling action of the connector. It is preferable for the swiveling action to take place between the anchoring mechanism and the interior of the receptacle.

FIG. 6 show the preferred shape of the anchoring mechanism. It is constructed as two component parts: the mechanism itself 600, and a threaded pin 610 which can be used to hand-tighten the anchoring mechanism to the side wall of the receptacle. It can alternatively be constructed as a single part without a pin. Again, the anchoring mechanism must be tall enough to keep it on the receptacle during use, preferably extending downward over the wall of the receptacle more than 2.5 cm.

The anchoring mechanism holds the hose such that the hose, as it comes over the top lip of the receptacle, angles downward into the receptacle. The exact angle of the hose as created by the anchoring mechanism is not essential, but the hose, as it enters the receptacle, should be below horizontal, preferably a depression angle of between 30 and 60 degrees below horizontal. FIGS. 1, 2, and 6 show an approximate depression angle of 45 degrees below horizontal.

It is important to note that the anchoring mechanism holds the hose coming from the concentrator in such a manner that the length of hose from the concentrator to the anchoring mechanism does not twist or otherwise move. The anchoring mechanism holds the hose from the concentrator steady so that the tubing swivel connector can do its job of allowing the hose to swivel and relieve kinks or twists in the hose collected within the receptacle. Hose motion should occur in the hose after it has left the anchoring mechanism, that is, between the roller system and the anchoring mechanism.

It should further be noted that in the preferred embodiment of this invention, the roller system would be controlled via a remote-control mechanism. The user could hold a small remote which would communicate wirelessly with the roller system control; the remote could be any of the commonly available ultrasonic, radio frequency, Bluetooth, phone-app controlled, Wi-Fi controlled, voice controlled, or consumer infrared wireless methods, including using IR LEDs. Wired remotes are disfavored because of the tripping hazard inherent in wires.

As an alternative to hanging the roller system and anchoring system on the receptacle, is conceivable that the roller system could be constructed so that it is incorporated with the receptacle wall or more permanently attached to the wall of a rigid receptacle. Likewise, as an alternative, a receptacle could be constructed to incorporate the detailed functions of the anchoring mechanism within its structure. However, incorporating in or permanently attaching these elements to a receptacle would tend to increase the overall costs, size, and increase complexity of manufacture and use.

All the aforementioned components could be of various sizes and of various substance and material and attached in such a way that would allow them to appropriately perform the required functions as described.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

Multiple further embodiments can be created by variously eliminating or adding any individual, non-essential element.

BRIEF SUMMARY OF THE INVENTION

The invention is a light-weight, powered system that allows a user to collect excess, loose fluid hose into a collection container and extract the hose as needed. The U.S. application Ser. No. 15/436,789, to Lucas, published 24 Aug. 2017, comprised a collection container and a non-spooling, powered roller system that could draw the excess hose into the collection container in such a way that hose remains connected to both the gas source and cannula and properly attached to the patient. In addition to allowing the patient—or another person—to collect the excess or loose hose, it allowed for extraction of the hose from the collection container as needed for movement.

The present invention describes improvements to the prior application, such that the roller system can be used with different containers and optimally manage the hose. The improvements include an anchoring mechanism to attach and align the hose to the container/receptacle, guides to align the hose into the roller system and prevent the hose from inadvertently leaving the receptacle during operation, and physical means to assure the roller system's proper angular alignment to the receptacle.

The invention claimed is:

1. A spool-less fluid hose collection system with rollers, comprising:
    a. a powered roller system attached to a receptacle, capable of pushing hose into said receptacle and pulling it from said receptacle;
    b. an anchoring mechanism attached to said receptacle and capable of holding said hose angled downward into said receptacle; and
    c. a wireless remote control that allows a user to control the operation of said roller system.

2. A spool-less fluid hose collection system with rollers, comprising:
    a. a powered roller system capable of being removably attached to a receptacle, capable of pushing a hose into said receptacle and pulling it from said receptacle;
    b. an anchoring mechanism capable of being removably attached to said receptacle and capable of holding said hose angled downward into said receptacle; and
    c. a wireless remote control that allows a user to control the operation of said roller system.

3. A hose collection system, as in claim 1, wherein said roller system is angled such that said hose, as it enters said receptacle, is angled downward into said receptacle.

4. A hose collection system, as in claim 1, wherein said anchoring mechanism is capable of holding a fluid hose swivel connector.

5. A hose collection system, as in claim 2, wherein said anchoring mechanism is capable of holding a fluid hose swivel connector.

6. A hose collection system, as in claim 2, wherein said anchoring mechanism is capable of being hung over the top lip of said receptacle.

7. A hose collection system, as in claim 2, wherein said roller system is capable of being hung over the top lip of said receptacle, opposite said anchoring mechanism.

8. A hose collection system, as in claim 2, wherein said roller system is angled such that said hose, as it enters said receptacle, is angled downward into said receptacle.

9. A spool-less fluid hose collection system with rollers, comprising:
    a. a powered roller system removably attached to a receptacle, capable of feeding a hose into said receptacle and pulling it from said receptacle;
    b. said roller system is controlled remotely and wirelessly by a user;
    c. said roller system is hung over a top lip of said receptacle using a bracket capable of fitting over said top lip of said receptacle;
    d. said roller system, when attached to said receptacle, is positioned such that said hose is angled downward into said receptacle; and
    e. an anchoring mechanism removably attached to said receptacle and capable of holding said hose adjacent to and angled downward into said receptacle;
    f. said anchoring mechanism is hung over said top lip of said receptacle; and
    g. said anchoring mechanism is capable of holding an oxygen tubing swivel connector.

10. A hose collection system, as in claim 9, wherein said roller system is angled using a brace attached to said roller system, said brace configured to position on the lower portion of said roller system away from the side wall of said receptacle, thereby angling said hose downward into said receptacle.

11. A hose collection system, as in claim 9, wherein the depression angle for said hose leading from said roller system downward into said receptacle is at least five degrees below horizontal.

12. A hose collection system, as in claim 9, wherein said roller system comprises a tubular guide which maintains the hose in a straight, unkinked, and untwisted state as it enters and exits said roller system from and into said receptacle.

13. A hose collection system, as in claim 12, wherein said tubular guide comprises a hollow shaft whose interior diameter changes such that it has an exit diameter wider than said shaft interior in diameter as it enters said roller system interior nearer the rollers.

14. A hose collection system, as in claim 9, further comprising a top guard which is positioned above said hose and prevents said hose from coiling over the top of said roller system during operation.

15. A hose collection system, as in claim 14, wherein said top guard is a roughly flat piece of material attached to said roller system over said hose.

* * * * *